United States Patent
Farr et al.

[11] Patent Number: 5,981,553
[45] Date of Patent: Nov. 9, 1999

[54] HETEROCYCLE SUBSTITUTED PROPENOIC ACID DERIVATIVES AS NMDA ANTAGONIST

[75] Inventors: Robert Farr, Loveland, Ohio; Boyd Harrison, Princeton Jct, N.J.; Philip Nyce, Millbury, Mass.

[73] Assignee: Hoechst Marion Roussel, Inc., Bridgewater, N.J.

[21] Appl. No.: 08/990,673

[22] Filed: Dec. 15, 1997

Related U.S. Application Data

[63] Continuation of application No. 08/809,442, Jul. 16, 1997, abandoned, which is a continuation of application No. 08/332,016, Oct. 31, 1994, Pat. No. 5,563,157.

[51] Int. Cl.$^6$ .................................................. A61K 31/44
[52] U.S. Cl. ............................................ 514/339; 514/414
[58] Field of Search ...................................... 514/339, 414

[56] References Cited

U.S. PATENT DOCUMENTS

| | | | |
|---|---|---|---|
| 5,106,847 | 4/1992 | Salituro et al. | 514/419 |
| 5,519,048 | 5/1996 | Salituro et al. | 514/419 |
| 5,714,500 | 2/1998 | Griffith et al. | 514/317 |

FOREIGN PATENT DOCUMENTS

| | | |
|---|---|---|
| 0568136 | 11/1993 | European Pat. Off. |
| 2266091 | 10/1993 | United Kingdom |
| 9216205 | 10/1992 | WIPO |
| 9321153 | 4/1993 | WIPO |
| 9427964 | 12/1994 | WIPO |

OTHER PUBLICATIONS

Salituro F.G. et al, Bioorganic & Medicinal Chem. Ltrs, vol. 1, No. 9 pp. 455–460, 1991.
Kemp, John A., TiPS—Jan. 1993, vol. 14, No. 1, pp. 20–25.
Schelkun, R.M. et Al, 33rd Nat'l Organic Chemistry Symposium Bozeman, MT—Jun., 1993 Abstract #B–73.
Thornber, Chemical Society Review, vol. 8, No. 4, 1979.

*Primary Examiner*—Jane Fan
*Attorney, Agent, or Firm*—Michael W. Ferrell

[57] ABSTRACT

The present invention is new 3-(heterocyclic)-propenoic acid derivatives and pharmaceutical compositions thereof. These new 3-(heterocyclic)-propenoic acid derivatives are useful as NMDA antagonist.

5 Claims, No Drawings

HETEROCYCLE SUBSTITUTED PROPENOIC ACID DERIVATIVES AS NMDA ANTAGONIST

This application is a continuation of application Ser. No. 08/809,442, filed Jul. 16, 1997, now abandoned, which is a continuation of application Ser. No. 08/332,016, filed Oct. 31, 1994, now U.S. Pat. No. 5,563,157, which is incorporated by reference.

The present invention is directed to a new class of excitatory amino acid antagonists and intermediates thereof. These new antagonists, heterocycle substituted propenoic acid derivatives, are useful as NMDA (N-methyl-D-aspartate) antagonists. They preferentially bind to the strychnine-insensitive glycine binding site on the NMDA receptor complex associated with the treatment of a number of disease states. Another aspect of the invention is directed to their use in treatment of a number of diseases as well as to pharmaceutical compositions containing these excitatory amino acid antagonists.

In accordance with the present invention, a new class of NMDA antagonists has been discovered which can be described by the formula:

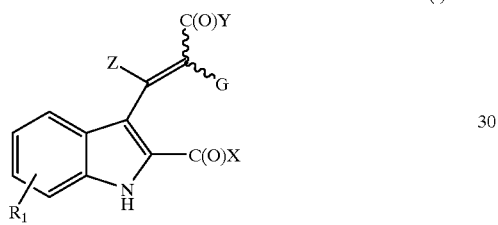

Formula (I)

wherein

Z is hydrogen or —CH$_3$;

X is represented by —OH, a physiologically acceptable ester, or a physiologically acceptable amide;

Y is represented by —OH, a physiologically acceptable ester, or a physiologically acceptable amide;

R$_1$ is represented by from 1 to 3 substituents independently chosen from the group: hydrogen, C$_1$–C$_4$ alkyl, C$_1$–C$_4$ alkoxy, halogen, —CF$_3$, or —OCF$_3$;

G is a radical chosen from the group

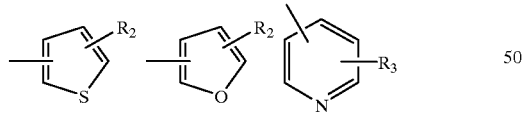

wherein

R$_2$ is represented by from 1 to 2 substituents independently chosen from the group: hydrogen or C$_1$–C$_4$ alkyl;

R$_3$ is represented by from 1 to 2 substituents independently chosen from the group: hydrogen, C$_1$–C$_4$ alkyl, C$_1$–C$_4$ alkoxy, or halogen;

and pharmaceutically acceptable addition salts thereof.

As used in this application:

a) the term "C$_1$–C$_4$ alkyl" refers to a branched or straight chained alkyl radical containing from 1–4 carbon atoms, such as methyl, ethyl, n-propyl, isopropyl, n-butyl, isobutyl, and the like;

b) the term "C$_1$–C$_4$ alkoxy" refers to a branched or straight chained alkoxy radical containing from 1–4 carbon atoms, such as methoxy, ethoxy, n-propoxy, isopropoxy, n-butoxy, isobutoxy, and the like;

c) the term "halogen" refers to a fluorine atom, a chlorine atom, a bromine atom, or a iodine atom;

d) the term "physiologically acceptable ester" refers to any non-toxic ester or any prodrug that allows the compounds of this application to function as NMDA antagonists: these physiologically acceptable esters may be chosen from but are not limited to compounds wherein X and Y may each independently be represented by —OR$_4$, —OCH$_2$OR$_4$ or —O—(CH$_2$)$_p$—NR$_5$R$_6$; wherein R$_4$ is represented by C$_1$–C$_4$ alkyl, phenyl, substituted phenyl, or an phenylalkyl substituent, such as benzyl, in which the phenyl ring may be optionally substituted; p is 2 or 3; and R$_5$ and R$_6$ are each independently represented by a C$_1$–C$_4$ alkyl or together with the adjacent nitrogen atom to form a ring —CH$_2$—CH$_2$—Z—CH$_2$—CH$_2$— wherein Z is a bond, O, S, or NR$_7$ in which R$_7$ is hydrogen or C$_1$–C$_4$ alkyl; such rings include but are not limited to piperidino, morpholino, thiomorpholino, piperazino, N-methylpiperazino, or pyrrolidino; and the pharmaceutically acceptable addition salts thereof;

e) the term "physiologically acceptable amide" refers to any non-toxic amide or any prodrug that allows the compounds of this application to function as NMDA antagonists: these physiologically acceptable amides may be chosen from, but are not limited to, compounds wherein X and Y may each independently be represented by —NR$_8$R$_9$; wherein R$_8$ and R$_9$ are each independently represented by hydrogen, phenyl, substituted phenyl, phenylalkyl, or a C$_1$–C$_4$ alkyl; or R$_8$ and R$_9$ are taken together with the adjacent nitrogen atom to form a ring —CH$_2$—CH$_2$—Z—CH$_2$—CH$_2$— wherein Z is a bond, O, S, or NR$_7$ in which R$_7$ is hydrogen or C$_1$–C$_4$ alkyl; such rings include but are not limited to piperidino, morpholino, thiomorpholino, piperazino, N-methylpiperazino, or pyrrolidino and the pharmaceutically acceptable addition salts thereof;

f) the designation

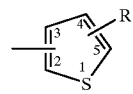

refers to a thienyl or thiophene and it is understood that the radical is attached at either the 2-position or 3-position, it is further understood that when the radical is attached at the 2-position the substituent or substituents represented by R can be attached in any of the 3, 4, or 5 positions, and that when the radical is attached at the 3-position the substituent or substituents represented by R can be attached in any of the 2, 4, or 5 positions;

g) the designation

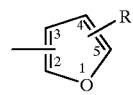

refers to a furyl, furanyl, or furan and it is understood that the radical is attached at either the 2-position or the 3-position, it is further understood that when the radical is attached at the 2-position the substituent or substituents represented by R can be attached in any of the 3, 4, or 5 positions, and that when the radical is attached at the 3-position the substituent or substituents represented by R can be attached in any of the 2, 4, or 5 positions;

h) the designation "C(O)" refers to a carbonyl group of the formula:

i) the designation

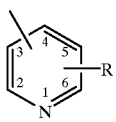

refers to a pyridine, pyridinyl, or pyridyl and it is understood that the radical can be attached at either the 2-position, 3-position, or 4-position, it is further understood that when the radical is attached at the 2-position the substituent or substituents represented by R can be attached in any of the 3, 4, 5, or 6 positions, that when the radical is attached at the 3-position the substituent or substituents represented by R can be attached in any of the 2, 4, 5, or 6 positions, and that when the radical is attached at the 4-position the substituent or substituents represented by R can be attached in any of the 2, 3, 5, or 6 positions;

j) the designation ∿∿ refers to a bond for which the stereochemistry is not designated;

k) the term "pharmaceutically acceptable addition salts" refers to either an acid addition salt or a basic addition salt.

The expression "pharmaceutically acceptable acid addition salts" is intended to apply to any non-toxic organic or inorganic acid addition salt of the base compounds represented by Formula (I) or any of its intermediates. Illustrative inorganic acids which form suitable salts include hydrochloric, hydrobromic, sulfuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by the Formula (I) or any of its intermediates. Illustrative bases which form suitable salts include alkali metals or alkaline-earth metals hydroxides such as, sodium, potassium, calcium, magnesium, or barium hydroxides; ammonia and aliphatic, cyclic, or aromatic organic amines such as methylamine, dimethylamine, trimethylamine, and picoline.

The compounds of Formula (I) exist as geometric isomers. Any reference in this application to one of the compounds of Formula (I) is meant to encompass either a specific geometrical isomer or a mixture of isomers. The specific isomers can be separated and recovered by techniques known in the art such as chromatography, and selective crystallization.

Illustrative examples of compounds encompassed by the present invention include:

(E)-2-Bromo-3-(1-p-toluenesulfonyl-2-carboethoxy-4,6-dichloroindol-3-yl)propenoic acid, t-butyl ester;

(Z)-2-Bromo-3-(1-p-toluenesulfonyl-2-carboethoxy-4,6-dichloroindol-3-yl)propenoic acid, t-butyl ester;

(E)-2-(Thien-3-yl)-3-(1-p-toluenesulfonyl-2-carboethoxy-4,6-dichloroindol-3-yl)propenoic acid, t-butyl ester;

(Z)-2-(Thien-3-yl)-3-(1-p-toluenesulfonyl-2-carboethoxy-4,6-dichloroindol-3-yl)propenoic acid, t-butyl ester;

(E)-2-(Thien-3-yl)-3-(1-p-toluenesulfonyl-2-carboethoxy-4,6-dichloroindol-3-yl)propenoic acid;

(Z)-2-(Thien-3-yl)-3-(1-p-toluenesulfonyl-2-carboethoxy-4,6-dichloroindol-3-yl)propenoic acid;

(E)-2-(Thien-2-yl)-3-(1-p-toluenesulfonyl-2-carboethoxy-4,6-dichloroindol-3-yl)propenoic acid, t-butyl ester;

(Z)-2-(Thien-2-yl)-3-(1-p-toluenesulfonyl-2-carboethoxy-4,6-dichloroindol-3-yl)propenoic acid, t-butyl ester;

(E)-2-(Thien-2-yl)-3-(1-p-toluenesulfonyl-2-carboethoxy-4,6-dichloroindol-3-yl)propenoic acid;

(Z)-2-(Thien-2-yl)-3-(1-p-toluenesulfonyl-2-carboethoxy-4,6-dichloroindol-3-yl)propenoic acid;

(E)-2-(Fur-2-yl)-3-(1-p-toluenesulfonyl-2-carboethoxy-4,6-dichloroindol-3-yl)propenoic acid, t-butyl ester;

(Z)-2-(Fur-2-yl)-3-(1-p-toluenesulfonyl-2-carboethoxy-4,6-dichloroindol-3-yl)propenoic acid, t-butyl ester;

(E)-2-(Fur-2-yl)-3-(1-p-toluenesulfonyl-2-carboethoxy-4,6-dichloroindol-3-yl)propenoic acid;

(Z)-2-(Fur-2-yl)-3-(1-p-toluenesulfonyl-2-carboethoxy-4,6-dichloroindol-3-yl)propenoic acid;

(E)-2-(Fur-3-yl)-3-(1-p-toluenesulfonyl-2-carboethoxy-4,6-dichloroindol-3-yl)propenoic acid, t-butyl ester;

(Z)-2-(Fur-3-yl)-3-(1-p-toluenesulfonyl-2-carboethoxy-4,6-dichloroindol-3-yl)propenoic acid, t-butyl ester;

(E)-2-(Fur-3-yl)-3-(1-p-toluenesulfonyl-2-carboethoxy-4,6-dichloroindol-3-yl)propenoic acid;

(Z)-2-(Fur-3-yl)-3-(1-p-toluenesulfonyl-2-carboethoxy-4,6-dichloroindol-3-yl)propenoic acid;

(E)-2-(Pyrid-4-yl)-3-(2-carboethoxy-4,6-dichloroindol-3-yl)propenonitrile;

(Z)-2-(Pyrid-4-yl)-3-(2-carboethoxy-4,6-dichloroindol-3-yl)propenonitrile;

(E)-2-(Pyrid-3-yl)-3-(2-carboethoxy-4,6-dichloroindol-3-yl)propenonitrile;

(Z)-2-(Pyrid-3-yl)-3-(2-carboethoxy-4,6-dichloroindol-3-yl)propenonitrile;

(E)-2-(Pyrid-2-yl)-3-(2-carboethoxy-4,6-dichloroindol-3-yl)propenonitrile;

(Z)-2-(Pyrid-2-yl)-3-(2-carboethoxy-4,6-dichloroindol-3-yl)propenonitrile;

(Z)-2-(Pyrid-4-yl)-3-(4,6-dichloroindol-3-yl-2-carboxylic acid)propenoic acid imide;

(Z)-2-(Pyrid-3-yl)-3-(4,6-dichloroindol-3-yl-2-carboxylic acid)propenoic acid imide;

(Z)-2-(Pyrid-2-yl)-3-(4,6-dichloroindol-3-yl-2-carboxylic acid)propenoic acid imide;

(E)-2-(Thien-3-yl)-3-(4,6-dichloroindol-3-yl-2-carboxylic acid)propenoic acid;
(Z)-2-(Thien-3-yl)-3-(4,6-dichloroindol-3-yl-2-carboxylic acid)propenoic acid;
(E)-2-(Thien-2-yl)-3-(4,6-dichloroindol-3-yl-2-carboxylic acid)propenoic acid;
(Z)-2-(Thien-2-yl)-3-(4,6-dichloroindol-3-yl-2-carboxylic acid)propenoic acid;
(E)-2-(Fur-2-yl)-3-(4,6-dichloroindol-3-yl-2-carboxylic acid)propenoic acid;
(Z)-2-(Fur-2-yl)-3-(4,6-dichloroindol-3-yl-2-carboxylic acid)propenoic acid;
(E)-2-(Fur-3-yl)-3-(4,6-dichloroindol-3-yl-2-carboxylic acid)propenoic acid;
(Z)-2-(Fur-3-yl)-3-(4,6-dichloroindol-3-yl-2-carboxylic acid)propenoic acid;
(E)-2-(Pyrid-4-yl)-3-(4,6-dichloroindol-3-yl-2-carboxylic acid)propenoic acid;
(Z)-2-(Pyrid-4-yl)-3-(4,6-dichloroindol-3-yl-2-carboxylic acid)propenoic acid;
(E)-2-(Pyrid-3-yl)-3-(4,6-dichloroindol-3-yl-2-carboxylic acid)propenoic acid;
(Z)-2-(Pyrid-3-yl)-3-(4,6-dichloroindol-3-yl-2-carboxylic acid)propenoic acid;
(E)-2-(Pyrid-2-yl)-3-(4,6-dichloroindol-3-yl-2-carboxylic acid)propenoic acid;
(Z)-2-(Pyrid-2-yl)-3-(4,6-dichloroindol-3-yl-2-carboxylic acid)propenoic acid.

The compounds of Formula (I) can be prepared as described in Reaction Scheme 1. All substituents, unless otherwise indicated, are previously defined. The reagents and starting materials are readily available to one of ordinary skill in the art.

REACTION SCHEME 1

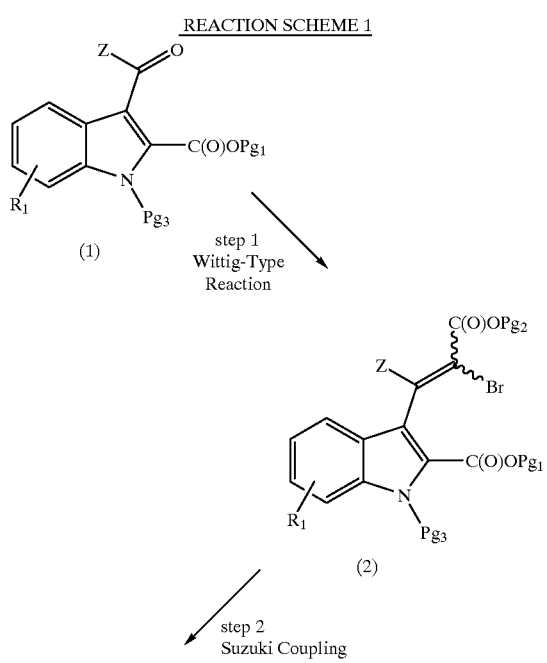

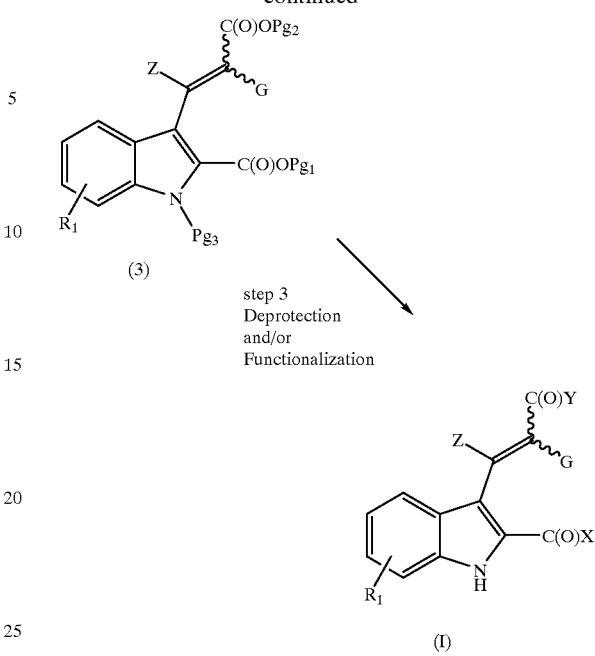

As disclosed in Reaction Scheme 1, the compounds of Formula (I) can be prepared by submitting an appropriate indole (1) to a Wittig-type reaction to give an 2-bromo-3-(indol-3-yl)propenoic acid ester of structure (2), a Suzuki coupling reaction with an appropriate arylboronic acid, $G-B(OH)_2$, to give compound (3), and deprotection and functionalization to give a compound of Formula (I). In preparing compounds of Formula (I) in which G is thienyl or furyl the method described in Reaction Scheme 1 is preferred.

In Reaction Scheme 1, step 1, an appropriate indole of structure (1) is contacted with an appropriate organophosphorous ylid in a Wittig-type reaction to give an 2-bromo-3-(indol-3-yl)propenoic acid ester of structure (2).

An appropriate indole compound of structure (1) is one in which $R_1$, and Z are as desired in the final product of Formula (I), $Pg_1$ is X as desired in the final product of formula (I) or gives rise after deprotection and functionalization as required to X as desired in the final product of Formula (I), and $Pg_3$ is a protecting group which is readily removed to give a final product of Formula (I) or allows for selective deprotection and functionalization as may be required to incorporate X and Y desired in the final product of Formula (I). Appropriate indoles of structure (1) are readily prepared by methods well known in the art, such as the Fischer indole synthesis, introduction of a 3-position carbonyl substituent, and protection of the indole nitrogen.

An appropriate organophosphorous ylid is one which converts the 3-position carbonyl of an indole of structure (1) to an 2-bromopropenoic acid ester of structure (2) in which $Pg_2$ is Y as desired in the final product of Formula (I) or gives rise after deprotection and functionalization as required to Y as desired in the final product of Formula (I). An appropriate organophosphorous ylid is formed by contacting an appropriate organophosphorous reagent, such as t-butyl diethylphosphonobromoacetate or ethyl diethylphosphonobromoacetate, with a suitable base, such as lithium diisopropylamide, sodium hydride, lithium bis(trimethylsilyl)amide or potassium t-butoxide. Appropriate organophosphorous reagents and the use of appropriate organophosphorous reagents is well known and appreciated in the art.

For example, an appropriate organophosphorous reagent is contacted with a suitable base, such as lithium diisopropylamide, sodium hydride, lithium bis(trimethylsilyl)amide or potassium t-butoxide. The ylid formation is carried out in a suitable solvent, such as tetrahydrofuran, benzene, or diethyl ether. The ylid formation is generally carried out at a temperature of from −78° C. to ambient temperature. An appropriate organophosphorous ylid is contacted with an appropriate indole of structure (1). The reaction is carried out in a suitable solvent, such as tetrahydrofuran, benzene, or diethyl ether. Generally, the reaction is carried out in the same solvent used to form the appropriate organophosphorous ylid. The reaction is carried out at temperatures of from −78° C. to the reflux temperature of the solvent. The reaction generally requires from 1 hour to 48 hours. The product can be isolated by techniques well known in the art, such as extraction and evaporation. The product can then be purified by techniques well known in the art, such as distillation, chromatography, or recrystallization.

In Reaction Scheme 1, step 2, an appropriate 2-bromo-3-(indol-3-yl)propenoic acid ester of structure (2) is contacted with an appropriate arylboronic acid in a Suzuki coupling to give a compound of structure (3). N. Miyaura et al., *J. Org. Chem.*, 51, 5467–5471 (1986); Y. Hoshino et al., *Bull. Chem. Soc. Japan*, 61, 3008–3010 (1988); N. Miyaura et al., *J. Am. Chem. Soc.*, 111, 314–321 (1989); W. J. Thompson et al., *J. Org. Chem.*, 53, 2052–2055 (1988); and T. I. Wallow and B. M. Novak, *J. Org. Chem.*, 59, 5034–5037 (1994).

An appropriate arylboronic acid, G-B(OH)$_2$, is one in which G is as desired in the final product of Formula (I). The preparation and use of arylboronic acids is well known and appreciated in the art. W. J. Thompson and J Gaudino, *J. Org. Chem.*, 49, 5237–5243 (1984). Arylboronic acids are frequently contaminated with their corresponding anhydrides which do not perform well in the Suzuki coupling. Material contaminated by detrimental amounts of anhydride can be converted to the corresponding acid by hydrolysis. The hydrolysis is performed, if required, by briefly boiling in water and the arylboronic acid is recovered by filtration.

For example, an appropriate 2-bromo-3-(indol-3-yl) propenoic acid ester of structure (2) is contacted with an appropriate arylboronic acid. The Suzuki coupling reaction is performed in a suitable solvent, such as toluene or tetrahydrofuran. The reaction is performed using from about 1.1 to about 3 molar equivalents of an appropriate arylboronic acid. The reaction is carried out in the presence of from about 1 to about 3 molar equivalents of a suitable base, such as potassium carbonate, sodium carbonate. The coupling is performed using a suitable palladium catalyst, such as tetrakis(triphenylphosphine)palladium (0), bis(acetonitrile) palladium (II) chloride, palladium (II) chloride, palladium (II) acetoacetate, and tris(dibenzylidneacetone)dipalladium (0). The suitable palladium catalyst chosen may be modified by the use of ligands, such as tri(fur-2-yl)phosphine and tri(o-toluene)phosphine. V. Farina and B. Krishnan, *J. Am. Chem. Soc.*, 113, 9586–9595 (1991). The coupling is performed at a temperature ranging from 0° C. to the refluxing temperature of the solvent. The coupling reactions depicted in Reaction Scheme 1 generally require from 6 hours to 14 days. The product (3) of the coupling reaction can be isolated and purified using techniques well known in the art. These techniques include extraction, evaporation, chromatography and recrystallization.

In Reaction Scheme 1, step 3, the compound of structure (3) obtained from the coupling reaction is deprotected and functionalized using techniques well known in the art to give compounds of Formula (I). These techniques include hydrolysis of esters, selective hydrolysis of esters, transesterification, removal of indole protecting groups, amidation of activated ester leaving groups, and esterification of activated ester leaving groups. As is appreciated to one skilled in the art, in Scheme 1 the number and order of deprotection, functionalization, and protection steps carried out will depend on the compound of Formula (I) which is desired as the product of Scheme 1. The selection, use, and removal of protecting groups utilizing suitable protecting groups such as those described in *Protecting Groups in Organic Synthesis* by T. Greene, Wiley-Interscience (1981) is well known and appreciated in the art.

As is disclosed in Reaction Scheme 1, step 3, the compounds of Formula (I) can be prepared by submitting a compound (3) to an appropriate functionalization reaction which introduces the appropriate functionality at the 2-position of the indole nucleus and/or at the 1-position of the propenoic acid thereby producing one of the desired compounds of Formula (I). In structure (3), Z, $R_1$, and G are as defined in Formula (I), $Pg_3$ is represented by an indole nitrogen protecting group, and $Pg_1$ and $Pg_2$ are each independently represented by groups such as, $C_1$–$C_4$ alkyl, or other active ester leaving groups known in the art, physiologically acceptable ester, or physiologically acceptable amide.

The functionalization reactions can be carried out using techniques well known in the art. For example, ester functionalities can be added to the 2-position of the indole nucleus and/or at the 1-position of the propenoic acid utilizing a variety of esterification techniques. One suitable esterification technique comprises contacting the appropriate compound of structure (3) in which $Pg_1$ and $Pg_2$ are $C_1$–$C_4$ alkyl functions with an excess of an appropriate alcohol. An appropriate alcohol is one which gives rise to groups X and Y as desired in the final product of Formula (I). The reaction is typically carried out in the presence of an excess of a base such as potassium carbonate. The reaction is typically carried out at a temperature ranging from room temperature to reflux for a period of time ranging from 1 hour to 24 hours. After the reaction is completed, the desired product of Formula (I) can be recovered by organic extraction and evaporation. It may then be purified by flash chromatography and recrystallization as is known in the art.

Amides can also be easily be prepared by contacting a compound of structure (3) in which $Pg_1$ and $Pg_2$ are $C_1$–$C_4$ alkyls with an excess of ammonia or a mono- or dialkylamine corresponding to X and Y desired in the final product of Formula (I). The reaction is carried out at a temperature of from 0–100° C. for a period of time ranging from 1–48 hours using the amine as solvent or in an inert solvent such as tetrahydrofuran. The resulting amide derivatives of Formula I can then be isolated and purified by techniques known in the art.

As is readily apparent to those skilled in the art, if X and Y are not both represented by the same function in the final product, then it will be necessary to carry out deprotection and functionalization reactions in a sequential manner utilizing suitable protecting groups such as those described in *Protecting Groups in Organic Synthesis*, T. Greene. This can be done utilizing techniques known to those skilled in the art; D. B. Bryan et al, *J. Am. Chem. Soc.*, 99, 2353 (1977); E. Wuensch, *Methoden der Organischen Chemie* (Houben-Weyl), E. Mueller, Ed., George Theime Verlag, Stuttgart, 1974, Vol. 15; M. G. Saulnierand and G. W. Gribble, *J. Org. Chem.*, 47, 2810 (1982); Y. Egawa et al, *Chem. Pharm. Bull.* 7, 896 (1963); R. Adams and L. H. Ulich, *J. Am. Chem. Soc.*, 42, 599 (1920); and J Szmuszkoviocz, *J. Org. Chem.*, 29, 834 (1964).

The formation and use of active ester leaving groups used in functionalizations reactions is well known and appreciated in the art. Active ester leaving groups include but are not limited to anhydrides, mixed anhydrides, acid chlorides, acid bromides, 1-hydroxybenzotriazole esters, 1-hydroxysuccinimide esters, or the activated intermediates formed in the presence of coupling reagents, such as dicyclohexylcarbodiimide, 1-(3-dimethyaminopropyl)-3-ethylcarbodiimide, and 2-ethoxy-1-ethoxycarbonyl-1,2-dihydroquinolone. Active ester leaving groups may be prepared and isolated before their use or may be prepared and used without isolation to form physiologically acceptable esters or physiologically acceptable amides.

For example, a compound of Formula (I) in which Y is a physiologically acceptable amide and X is a physiologically acceptable ester or —OH can be prepared from a compound of structure (3) in which $Pg_2$ is t-butyl and $Pg_1$ is a physiologically acceptable ester other than t-butyl or a hydrolyzable ester. Selective removal of the t-butyl group gives a compound of structure (3) in which $Pg_2$ is —OH and $Pg_1$ is a physiologically acceptable ester other than t-butyl or a hydrolyzable ester which can be amidated through the formation of an activated ester leaving group followed by the addition of an suitable amine as is well known in the art. A suitable amine is one which gives a physiologically acceptable amide, Y, as is desired in the final product of Formula (I). Suitable amines include but are not limited to methylamine, dimethylamine, ethylamine, diethylamine, propylamine, butylamine, aniline, 4-chloroaniline, N-methylaniline, benzylamine, phenethylamine, morpholine, piperazine, piperidine, N-methylpiperazine, thiomorpholine, pyrrolidine, and N-methylbenzylamine. Formation of an active ester leaving group requires protection of the indole NH using a suitable protecting group, such as benzenesulfonyl, p-toluenesulfonyl, trimethylsilyl, trimethylsilylethoxymethyl, and the like. Further functionalization or hydrolysis gives a compound of Formula (I) in which Y is a physiologically acceptable amide and X is a physiologically acceptable ester or —OH. After the functionalization removal of the indole NH protecting group gives a compound of Formula (I).

Similarly, a compound of Formula (I) in which X is a physiologically acceptable amide and Y is a physiologically acceptable ester or —OH can be prepared from a compound of structure (3) in which $Pg_1$ is t-butyl and $Pg_2$ is a physiologically acceptable ester other than t-butyl or a hydrolyzable ester.

The compounds of Formula (I) in which X and Y are —OH can be prepared from a compound of structure (3) in which $Pg_1$ and $Pg_2$ are $C_1$–$C_4$ alkoxy, or an activated ester leaving group by deprotection using a molar excess of a suitable reagent, such as lithium hydroxide, sodium hydroxide, potassium hydroxide, sodium bicarbonate, sodium carbonate, or potassium carbonate with lithium hydroxide, sodium hydroxide, potassium hydroxide being preferred and lithium hydroxide being most preferred. These deprotections are carried out in a suitable solvent, such as mixtures of tetrahydrofuran and water, or water. The reaction is typically carried out at a temperature ranging from room temperature to reflux for a period of time ranging from 1 hour to 24 hours. After the reaction is completed, the desired product of Formula (I) can be recovered by techniques well known in the art, such as evaporation, precipitation by adjustment of the pH of the solution with a suitable acid such as hydrochloric acid, sodium bisulfate, potassium bisulfate, acetic acid, etc., extraction, and recrystallization.

Alternately, some of the compounds of Formula (I) can be prepared as described in Reaction Scheme 2. All substituents, unless otherwise indicated, are previously defined. The reagents and starting materials are readily available to one of ordinary skill in the art.

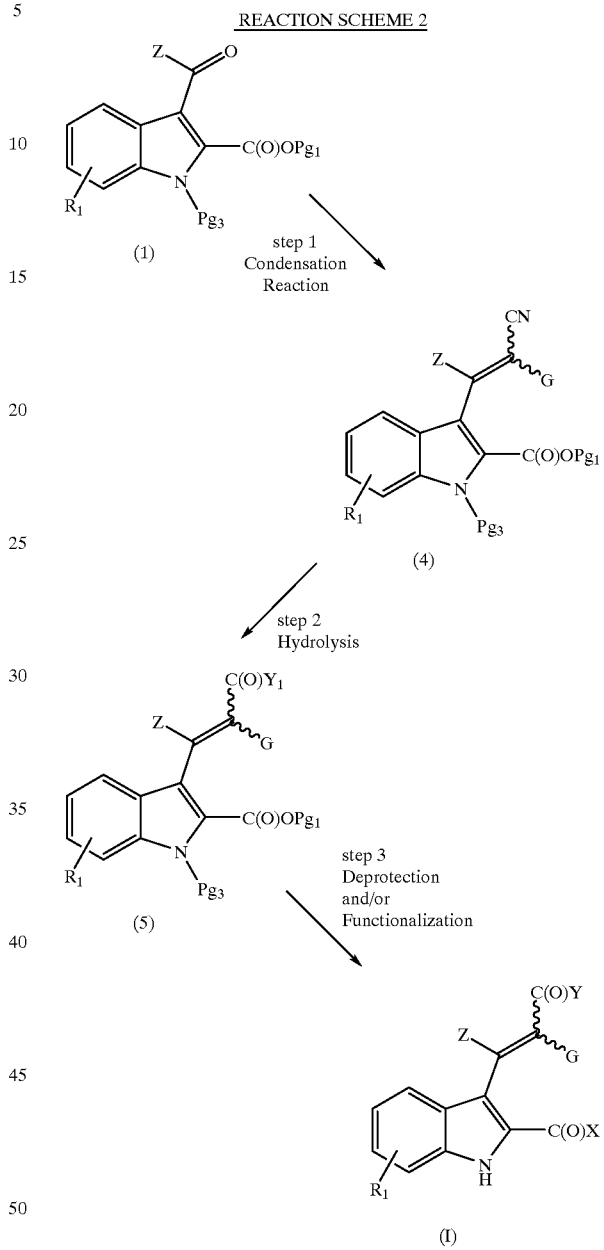

As disclosed in Reaction Scheme 2, the compounds of Formula (I) can be prepared by submitting an appropriate indole (1) to a condensation reaction to give an 2-aryl-3-(indol-3-yl)propenonitrile of structure (4), hydrolysis to give compound (5), and deprotection and/or functionalization to give a compound of formula (I). In preparing compounds of Formula (I) in which G is pyridyl the method described in reaction Scheme 2 is preferred.

In Reaction Scheme 2, step 1, an appropriate indole of structure (1) is contacted with an appropriate arylacetonitrile in a condensation reaction to give a 2-aryl-3-(indol-3-yl)propenonitrile of structure (4).

An appropriate indole compound of structure (1) is one in which $R_1$, and Z are as desired in the final product of Formula (I), $Pg_1$ is X as desired in the final product of formula (I) or gives rise after deprotection and functionalization as required to X as desired in the final product of Formula (I), and $Pg_3$ is hydrogen or a protecting group which is readily removed to give a final product of Formula (I) or allows for selective deprotection and functionalization as may be required to incorporate X and Y desired in the final product of Formula (I). Appropriate indoles of structure (1) are readily prepared by methods well known in the art, such as the Fischer indole synthesis, introduction of a 3-position carbonyl substituent, and if required, protection of the indole nitrogen.

An appropriate arylacetonitrile, G—CH$_2$—CN, is one in which G is as desired in the final product of Formula (I).

For example, an appropriate indole of structure (1) is contacted with an appropriate arylacetonitrile. The reaction is carried out in a suitable solvent, such as tetrahydrofuran, ethanol, or methanol. The reaction is carried out using a suitable base, such as piperidine, triethylamine, sodium hydride, or sodium carbonate. The reaction is generally carried out at temperatures of from ambient temperature to the refluxing temperature of the solvent. The reaction generally requires from 1 hour to 120 hours. The product can be isolated by techniques well known in the art, such as extraction and evaporation. The product can then be purified by techniques well known in the art, such as distillation, chromatography, or recrystallization.

In Reaction Scheme 2, step 2, an appropriate 2-aryl-3-(indol-3-yl)propenonitrile of structure (4) is hydrolyzed to give a compound of structure (5) in which $Y_1$ is —OH or —NH$_2$. It is understood that such hydrolyses may be carried out in a number of steps through intermediates, such as imides.

In Reaction Scheme 2, step 3, the compound of structure (5) obtained from the hydrolysis reaction may be optionally protected, deprotected, and functionalized using techniques well known in the art and described in Reaction Scheme 1, step 3, to give compounds of Formula (I). These techniques include formation of esters to give a compound of structure (3), hydrolysis of esters, selective hydrolysis of esters, transesterification, removal of indole protecting groups, amidation of activated ester leaving groups, and esterification of activated ester leaving groups.

The following preparations represent typical procedures for preparing starting materials used in the examples. The following examples present typical syntheses as described in Reaction Scheme 1, and Reaction Scheme 2. These preparations and examples are understood to be illustrative only and are not intended to limit the scope of the invention in any way. As used in the following preparations and examples, the following terms have the meanings indicated: "kg" refers to kilograms, "g" refers to grams, "mg" refers to milligrams, "mol" refers to moles, "mmol" refers to millimoles, "L" refers to liters, "mL" refers to milliliters, "°C." refers to degrees Celsius, "M" refers to molar, "mp" refers to melting point, "dec" refers to decomposition.

PREPARATION 1.1

3-Formyl-1-p-toluenesulfonyl-2-carboethoxy-4,6-dichloroindole

Combine 3,5-dichlorophenylhydrazine (300 g) and ethanol (2 L). Add ethyl pyruvate (153.6 mL) and sulfuric acid (25 mL). After 3 hours, evaporate in vacuo to obtain a residue. Cover the residue with ethyl acetate and water. Add solid sodium bicarbonate until the aqueous layer is neutralized. Separate the layers and extract the aqueous layer with ethyl acetate. Combine the organic layers, dry over MgSO$_4$, filter, and evaporate in vacuo to give ethyl pyruvate-3,5-dichlorophenylhydrazone.

Combine ethyl pyruvate-3,5-dichlorophenylhydrazone (100 g) and polyphosphoric acid (2 kg). Heat on a stream bath. After 5 hours, stop the heating and slowly add ice (100 g) to thin the solution. Pour the reaction mixture onto ice to give an aqueous suspension. Extract the aqueous suspension three times with ethyl acetate. Combine the organic layers, dry over MgSO$_4$, filter, and evaporate in vacuo to give a solid. Triturate the solid with diethyl ether, filter, and dry to give 2-carboethoxy-4,6-dichloroindole.

Combine 2-carboethoxy-4,6-dichloroindole (20.0 g, 0.077 mol), and dimethylformamide (9.0 mL, 0.117 mol) in dichloroethane (100 mL). Add phosphoryl chloride (18.0 g, 0.117 mmol). Heat to reflux. After 3.5 hours, cool the reaction mixture to ambient temperature to obtain a solid. Collect the solid by filtration, rinse with water. Combine the solid with aqueous 1 M sodium acetate solution and stir. After 1 hour, filter, rinse with water, and dry to give 3-formyl-2-carboethoxy-4,6-dichloroindole.

Combine 3-formyl-2-carboethoxy-4,6-dichloroindole (46.3 g, 162 mmol) and anhydrous potassium carbonate (44.9 g, 325 mmol) in dimethylformamide (600 mL). Add p-toluenesulfonyl chloride (42.9 g, 225 mmol). After 18 hours, pour the reaction mixture into water (3 L) and stir to give a solid. Filter, rinse with water and diethyl ether, and recrystallize from acetonitrile/dichloroethane to give the title compound.

PREPARATION 1.2

3-Formyl-1-p-toluenesulfonyl-2-carboethoxy-4,6-dichloroindole

Combine 2-carboethoxy-4,6-dichloroindole (10.0 g, 0.039 mol), and dimethylformamide (4.5 mL, 0.057 mol) in dichloroethane (20 mL). Add phosphoryl chloride (8.9 g, 0.058 mmol). Heat to 80° C. After 18 hours, cool the reaction mixture to ambient temperature and combine with aqueous 1 M sodium acetate solution and stir. After 18 hours, filter, rinse with water, and dry to give 3-formyl-2-carboethoxy-4,6-dichloroindole.

React 3-formyl-2-carboethoxy-4,6-dichloroindole with p-toluenesulfonyl chloride as describe in Preparation 1.1 to give the title compound.

PREPARATION 2

3-Acetyl-1-p-toluenesulfonyl-2-carboethoxy-indole

Prepare by the method of Preparation 1.1. using 3-acetyl-2-carboethoxy-indole, Y. Murakami, et al., *Heterocycles* 22, 241–244 (1984) and Y. Murakami, et al., *Heterocycles* 14, 1939–1941 (1980) and p-toluenesulfonyl chloride to give the title compound.

PREPARATION 3

Furan-2-boronic acid

According to the method of M. J. Arco et al., *J. Org. Chem.*, 41 2075–2083 (1976) combine furan (10 g, 147 mmol) and tetrahydrofuran ((50 mL). Cool to −30° C. Add a solution of n-butyl lithium (59 mL, 2.5 M in hexane, 147 mmol). After the addition is complete, warm the reaction mixture to −15° C. After 4 hours, add triisopropylborate (56.4 g, 300 mmol) and warm to ambient temperature. After 24 hours, partition the reaction mixture between 0.5 M aqueous hydrochloric acid solution and diethyl ether. Separate the organic layer, dry over MgSO$_4$, filter, and dry in vacuo to give a residue. Recrystallize the residue from water, filter, and dry to give the title compound.

PREPARATION 4

Furan-3-boronic acid

Cool a solution of n-butyl lithium (25.4 mL, 2.5 M in hexane, 63.6 mmol) to −78° C. Add a solution 3-bromofuran (7.8 g, 53 mmol) in tetrahydrofuran (20 mL). After 10 minutes, add triisopropylborate (20 g, 106 mmol) and warm to ambient temperature. After 24 hours, partition the reaction mixture between 0.5 M aqueous hydrochloric acid solution and diethyl ether. Separate the organic layer, dry over MgSO$_4$, filter, and dry in vacuo to give a residue. Recrystallize the residue from water, filter, and dry to give the title compound.

PREPARATION 5 t-Butyl diethylphosphonobromoacetate

Combine sodium hydroxide (65 g, 1.6 mol) and water (195 mL). Cool to −10° C. Add dropwise, bromine (42 mL, 0.81 mol) at such a rate that the temperature of the reaction does not rise above 0° C. Add t-butyl diethylphosphonoacetate (46.5 g, 184 mmol) at such a rate that the temperature of the reaction does not rise above 0° C. After 90 minutes, extract the reaction mixture three times with chloroform. Combine the organic layers and extract with water, dry over MgSO$_4$, filter, and evaporate in vacuo to give t-butyl diethylphosphonodibromoacetate.

Combine t-butyl diethylphosphonodibromoacetate (75.6 g, 184 mmol) and isopropanol (190 mL). Cool to 0° C. Add a solution of tin (II) chloride (33.2 g, 175 mmol) in water (190 mL). After the addition is complete, warm to ambient temperature. After 1 hour, extract the reaction mixture three times with chloroform. Combine the organic layers and extract with water, dry over MgSO$_4$, filter, and evaporate in vacuo to give the title compound.

PREPARATION 6

(E) and (Z)-2-bromo-3-(1-p-toluenesulfonyl-2-carboethoxy-4,6-dichloroindol-3-yl)propenoic acid, t-butyl ester Combine t-butyl diethylphosphonobromoacetate (45.4 g, 137 mmol) and tetrahydrofuran (550 mL). Cool to −78° C. Add dropwise a solution of lithium bis(trimethylsilyl)amide (137 mL, 1.0 M in tetrahydrofuran, 137 mmol). Add, portionwise over 30 minutes, 3-formyl-1-p-toluenesulfonyl-2-carboethoxy-4,6-dichloroindole (38.4 g, 87.2 mmol). After the addition is complete, warm to ambient temperature. After 18 hours, add water and evaporate in vacuo to remove the tetrahydrofuran. Extract with dichloromethane. Dry the organic layer over MgSO$_4$, filter, and evaporate in vacuo to give a residue. Recrystallize the powder from ethyl acetate/cyclohexane, filter, and dry to give the (Z)-isomer: mp 131–132° C. $^1$H NMR (CDCl$_3$) δ 8.21 (s, 1H), 7.95 (m, 3H), 7.30 (m, 3H), 4.42 (q, 2H, J=7.2 Hz), 2.41 (s, 3H), 1.56 (s, 9H), 1.36 (t, 3H, J=7.15 Hz). Elemental Analysis calculated for C$_{25}$H$_{24}$BrCl$_2$NO$_6$S: C, 48.64; H, 3.92; N, 2.26. Found: C, 48.44; H, 3.90; N, 2.22.

Chromatograph a mixture of (E) and (Z)-isomers on silica gel. Evaporate the early eluting fractions to give a residue enriched in the (E)-isomer. Recrystallize the residue from diethyl ether/pentane and cool to −20° C. to give the (E)-isomer. $^1$H NMR (CDCl$_3$) δ 7.99 (d, 1H, J=1.7 Hz), 7.96 (d, 2H, J=8.7 Hz), 7.50 (s, 1H), 7.33 (d, 2H, J=8.7 Hz), 7.27 (d, 1H, J=1.7 Hz), 4.42 (q, 2H, J=7.2 Hz), 2.42 (s, 3H), 1.39 (t, 3H, J=7.2 Hz), 1.00 (s, 9H).

PREPARATION 7

(Z)-2-bromo-3-methyl-3-(1-p-toluenesulfonyl-2-carboethoxy-indol-3-yl)propenoic acid, t-butyl ester Prepare by the method of Preparation 6 using 3-acetyl-1-p-toluenesulfonyl-2-carboethoxy-indole to give the title compound.

EXAMPLE 1

Preparation of (E)-2-(Thien-3-yl)-3-(4,6-dichloroindol-3-yl-2-carboxylic acid)propenoic acid 1.1 Synthesis of (E)-2-(Thien-3-yl)-3-(1-p-toluenesulfonyl-2-carboethoxy-4,6-dichloroindol-3-yl)propenoic acid, t-butyl ester

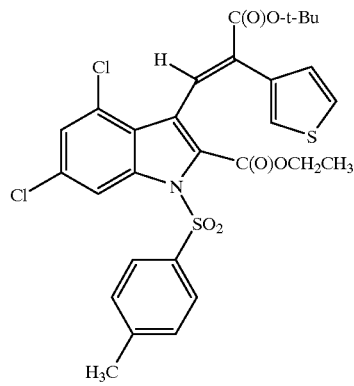

Combine tris(dibenzylideneacetone)dipalladium(0) (204 mg, 0.223 mmol) and tri-(fur-2-yl)phosphine (413 mg, 1.78 mmol) in tetrahydrofuran (60 mL). After 5 minutes, add (Z)-2-bromo-3-(1-p-toluenesulfonyl-2-carboethoxy-4,6-dichloroindol-3-yl)propenoic acid, t-butyl ester (1.85 g, 3.0 mmol), thiophene-3-boronic acid (1.16 g, 9.1 mmol), and powdered potassium carbonate (1.27 g, 9.2 mmol). Heat to 60° C. After 6 days, add thiophene-3-boronic acid (744 mg, 5.8 mmol), tri-(fur-2-yl)phosphine (206 mg, 0.887 mmol), tris(dibenzylideneacetone)dipalladium(0) (102 mg, 0.111 mmol), and powdered Potassium carbonate (800 mg, 5.80 mmol). After 3 more days, dilute the reaction mixture with cyclohexane (60 mL) and chromatograph on silica gel eluting with 3/1 cyclohexane/ether to give the title compound. $^1$H NMR (CDCl$_3$) δ 7.94 (d, 1H, J=1.7 Hz), 7.74 (d, 2H, J=8.4 Hz), 7.72 (s, 1H), 7.26 (d, 2H, J=8.0 Hz), 7.24 (d, 1H, J=1.7 Hz), 7.03 (d, 1H, J=4.4 Hz), 7.02 (d, 1H, J=1.5 Hz), 6.77 (dd, 1H, J=4.7, 1.6 Hz), 4.20 (q, 2H, J=7.15 Hz), 2.40 (s, 3H), 1.55 (s, 9H), 1.28 (t, 3H, J=7.15 Hz).

1.2 Synthesis of (E)-2-(Thien-3-yl)-3-(1-p-toluenesulfonyl-2-carboethoxy-4,6-dichloroindol-3-yl)propenoic acid

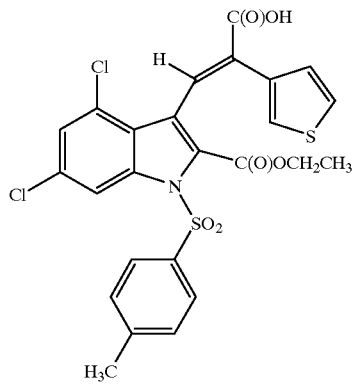

Combine (E)-2-(thien-3-yl)-3-(1-p-toluenesulfonyl-2-carboethoxy-4,6-dichloroindol-3-yl)propenoic acid, t-butyl ester and trifluoroacetic acid (10 mL). After 45 min, evaporate in vacuo to obtain a residue. Dissolve the residue in ethyl acetate and extract with water. Evaporate the organic layer in vacuo to obtain a residue. Triturate with pentane containing a small amount of ether to give a solid. Recrystallize the solid from cyclohexane/ethyl acetate, filter, and dry to give the title compound: mp 197–200° C. (dec); $^1$H NMR (CDCl$_3$) δ 8.00 (s, 1H), 7.95 (d, 1H, J=1.7 Hz), 7.74 (d, 2H, J=8.5 Hz), 7.27 (d, 2H, J=8.5 Hz), 7.25 (d, 1H, J=1.7 Hz), 7.08 (d, 1H, J=2.8 Hz), 7.08 (d, 1H, J=3.6 Hz), 6.81 (dd, 1H, J=3.6, 2.8 Hz), 4.22 (q, 2H, J=7.2 Hz), 2.40 (s, 3H), 1.28 (t, 3H, J=7.2 Hz); $^1$H NMR (DMSO-d$_6$) δ 13.07 (br s, 1H), 7.88 (d, 1H, J=1.7 Hz), 7.74 (d, 2H, J=8.4 Hz), 7.66 (s, 1H), 7.57 (d, 1H, J=1.7 Hz), 7.44 (d, 2H, J=8.4 Hz), 7.27 (dd, 1H, J=5.0, 2.9 Hz), 7.09 (dd, 1H, J=2.9, 1.2 Hz), 6.63 (dd, 1H, J=5.0, 1.2 Hz), 4.11 (q, 2H, J=7.1 Hz), 2.36 (s, 3H), 1.14 (t, 3H, J=7.1 Hz). Elemental Analysis calculated for C$_{25}$H$_{19}$Cl$_2$NO$_6$S$_2$: C, 53.20; H, 3.39; N, 2.48. Found: C, 52.80; H, 3.19; N, 2.29.

1.3 Synthesis of (E)-2-(Thien-3-yl)-3-(4,6-dichloroindol-3-yl-2-carboxylic acid)propenoic acid

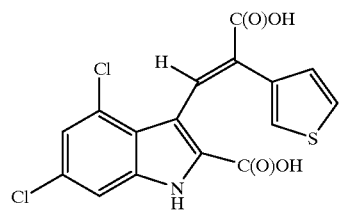

Combine (E)-2-(thien-3-yl)-3-(1-p-toluenesulfonyl-2-carboethoxy-4,6-dichloroindol-3-yl)propenoic acid (1.15 g, 2.03 mmol) and lithium hydroxide hydrate (288 mg, 6.86 mmol) in 1/1 tetrahydrofuran/water (22 mL). Heat to reflux. After 4 hours, cool to ambient temperature, evaporate in vacuo to remove most of the tetrahydrofuran, dilute with water, and acidify using an aqueous sodium bisulfate solution. Extract with ethyl acetate. Dry the organic layer over MgSO$_4$, filter, and evaporate in vacuo to give a solid. Recrystallize the solid from cyclohexane/ethyl acetate/acetone, filter, and dry in vacuo with heat to give the title compound: mp 228–232° C. (dec). $^1$H NMR (DMSO-d$_6$) δ 13.3 (br s, 1H), 12.8 (br s, 1H), 12.24 (s, 1H), 8.01 (s, 1H), 7.37 (d, 1H, J=1.7 Hz), 7.20 (dd, 1H, J=5.0, 3.0 Hz), 7.12 (d, 1H, J=1.7 Hz), 7.03 (dd, 1H, J=3.0, 1.2 Hz), 6.66 (dd, 1H, J=5.0, 1.2 Hz). Elemental Analysis calculated for C$_{16}$H$_9$Cl$_2$NO$_4$S: C, 50.28; H, 2.37; N, 3.66. Found: C, 50.01; H, 2.56; N, 3.57.

EXAMPLE 2

Preparation of (E)-2-(Thien-2-yl)-3-(4,6-dichloroindol-3-yl-2-carboxylic acid)propenoic acid

2.1 Synthesis of (E)-2-(Thien-2-yl)-3-(1-p-toluenesulfonyl-2-carboethoxy-4,6-dichloroindol-3-yl)propenoic acid, t-butyl ester

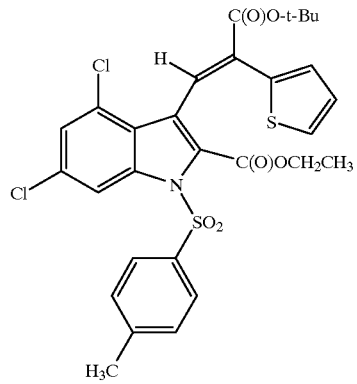

Combine tris(dibenzylideneacetone)dipalladium(0) (412 mg, 0.450 mmol) and tri-(fur-2-yl)phosphine (837 mg, 3.60 mmol) in tetrahydrofuran (60 mL). After 5 minutes, add (Z)-2-bromo-3-(1-p-toluenesulfonyl-2-carboethoxy-4,6-dichloroindol-3-yl)propenoic acid, t-butyl ester (1.85 g, 3.0 mmol), thiophene-2-boronic acid (1.12 g, 9.20 mmol), and powdered potassium carbonate (1.27 g, 9.2 mmol). Heat to 60° C. After 8 days, dilute the reaction mixture with cyclohexane (120 mL) and chromatograph on silica gel eluting with 3/1 cyclohexane/ether to give the title compound. $^1$H NMR (CDCl$_3$) δ 7.97 (d, 1H, J=1.7 Hz), 7.80 (d, 2H, J=8.5 Hz), 7.64 (s, 1H), 7.27 (d, 2H, J=8.5 Hz), 7.23 (d, 1H, J=1.7 Hz), 7.16 (dd, 1H, J=5.1, 1.2 Hz), 6.83 (dd, 1H, J=3.7, 1.2 Hz), 6.75 (dd, 1H, J=5.1, 3.7 Hz), 4.24 (q, 2H, J=7.1 Hz), 2.39 (s, 3H), 1.57 (s, 9H), 1.26 (t, 3H, J=7.1 Hz).

2.2 Synthesis of (E)-2-(Thien-2-yl)-3-(1-p-toluenesulfonyl-2-carboethoxy-4,6-dichloroindol-3-yl)propenoic acid

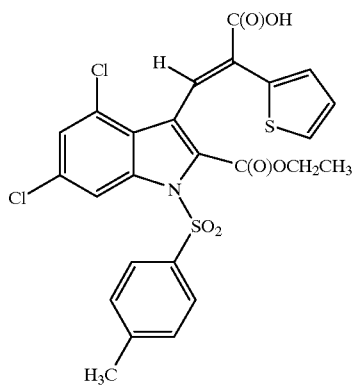

Combine (E)-2-(thien-2-yl)-3-(1-p-toluenesulfonyl-2-carboethoxy-4,6-dichloroindol-3-yl)propenoic acid, t-butyl ester and formic acid (96%, 20 mL). After 2 hours, evaporate in vacuo to obtain a residue. Triturate with pentane containing a small amount of diethyl ether to obtain a solid. Recrystallize the solid from cyclohexane/ethyl acetate/acetone, filter, and dry to give the title compound: mp 184–187° C. (dec). $^1$H NMR (DMSO-$d_6$) δ 13.2 (br s, 1H), 7.92 (d, 1H, J=1.7 Hz), 7.80 (d, 2H, J=8.4 Hz), 7.60 (s, 1H), 7.57 (d, 1H, J=1.7 Hz), 7.44 (d, 2H, J=8.4 Hz), 7.40 (dd, 1H, J=4.7, 1.5 Hz), 6.84–6.8 (m, 2H), 4.14 (q, 2H, J=7.1 Hz), 2.37 (s, 3H), 1.13 (t, 3H, J=7.1 Hz). Elemental Analysis calculated for $C_{25}H_{19}Cl_2NO_6S_2$: C, 53.20; H, 3.39; N, 2.48. Found: C, 53.30; H, 3.40; N, 2.41.

2.3 Synthesis of (E)-2-(Thien-2-yl)-3-(4,6-dichloroindol-3-yl-2-carboxylic acid)propenoic acid

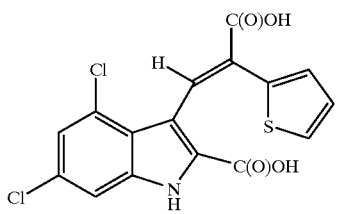

Combine (E)-2-(thien-2-yl)-3-(1-p-toluenesulfonyl-2-carboethoxy-4,6-dichloroindol-3-yl)propenoic acid (1.24 g, 2.20 mmol) and lithium hydroxide hydrate (313 mg, 7.46 mmol) in 1/1 tetrahydrofuran/water (24 mL). Heat to reflux. After 4 hours, cool to ambient temperature, evaporate in vacuo to remove most of the tetrahydrofuran, dilute with water, and acidify using an aqueous sodium bisulfate solution. Extract with ethyl acetate. Dry the organic layer over $MgSO_4$, filter, and evaporate in vacuo to give a solid. Recrystallize the solid from cyclohexane/ethyl acetate/acetone, filter, and dry to give the title compound: mp 239–244° C. (dec). $^1$H NMR (DMSO-$d_6$) δ 7.92 (s, 1H), 7.38 (d, 1H, J=1.7 Hz), 7.28 (dd, 1H, J=5.1, 1.2 Hz), 7.12 (d, 1H, J=1.7 Hz), 6.87 (dd, 1H, J=3.7, 1.2 Hz), 6.77 (dd, 1H, J=5.1, 3.7 Hz). Elemental Analysis calculated for $C_{16}H_9Cl_2NO_4S$: C, 50.28; H, 2.37; N, 3.66. Found: C, 50.31; H, 2.58; N, 3.51.

EXAMPLE 3

Preparation of (E)-2-(Fur-2-yl)-3-(4,6-dichloroindol-3-yl-2-carboxylic acid)propenoic acid

3.1 Synthesis of (E)-2-(Fur-2-yl)-3-(1-p-toluenesulfonyl-2-carboethoxy-4,6-dichloroindol-3-yl)propenoic acid, t-butyl ester

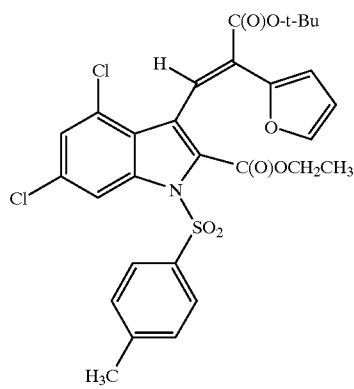

Combine (Z)-2-bromo-3-(1-p-toluenesulfonyl-2-carboethoxy-4,6-dichloroindol-3-yl)propenoic acid, t-butyl ester (1.00 g, 1.6 mmol), furan-2-boronic acid (0.27 g, 2.4 mmol), and cesium carbonate (1.00 g, 3.2 mmol) in toluene (15 mL). Sparge with nitrogen for 15 minutes. Add tetrakis(triphenylphosphine)palladium(0) (50 mg). Heat to 90° C. After 3 days, partition the reaction mixture between ethyl acetate and water. Separate the layers. Dry the organic layer over $MgSO_4$, filter, and evaporate in vacuo to give a reside. Chromatograph the residue on silica gel eluting with 15% diethyl ether/hexane to give the title compound.

3.2 Synthesis of (E)-2-(Fur-2-yl)-3-(1-p-toluenesulfonyl-2-carboethoxy-4,6-dichloroindol-3-yl)propenoic acid

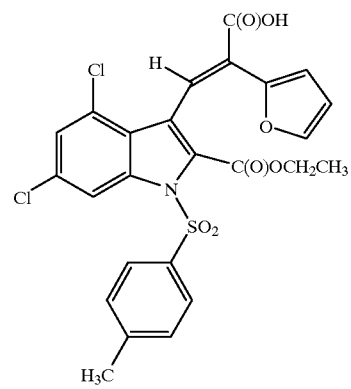

Combine (E)-2-(fur-2-yl)-3-(1-p-toluenesulfonyl-2-carboethoxy-4,6-dichloroindol-3-yl)propenoic acid, t-butyl ester (112 mg, 0.19 mmol) and trifluoroacetic acid (2 mL) in dichloromethane (5 mL). After 2 hours, evaporate in vacuo, add dichloromethane and evaporate in vacuo to give the title compound.

3.3 Synthesis of (E)-2-(Fur-2-yl)-3-(4,6-dichloroindol-3-yl-2-carboxylic acid)propenoic acid

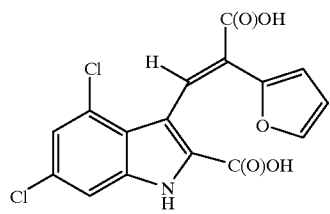

Combine (E)-2-(fur-2-yl)-3-(1-p-toluenesulfonyl-2-carboethoxy-4,6-dichloroindol-3-yl)propenoic acid (0.1 g, 0.18 mmol) and an aqueous solution of lithium hydroxide (2 mL, 1 M in water, 2 mmol) in tetrahydrofuran (2 mL). Heat to reflux. After 24 hours, cool to ambient temperature, dilute with water, and acidify using aqueous hydrochloric acid solution to give a solid. Filter, and dry in vacuo to give the title compound: mp 237–239° C. (dec). $^1$H NMR (DMSO-$d_6$) δ 13.3 (bs, 1H), 12.95 (bs, 1H), 12.32 (s, 1H), 7.90 (s, 1H), 7.40 (d, 1H, J=1.8 Hz), 7.29 (dd, 1H, J=1.7, 0.6 Hz), 7.12 (d, 1H, J=1.8 Hz), 6.43 (dm, 1H, J=3.4 Hz), 6.31 (dd, 1H, J=3.4, 1.8 Hz).

EXAMPLE 4

Preparation of (E)-2-(Fur-3-yl)-3-(4,6-dichloroindol-3-yl-2-carboxylic acid)propenoic acid

4.1 Synthesis of (E)-2-(Fur-3-yl)-3-(1-p-toluenesulfonyl-2-carboethoxy-4,6-dichloroindol-3-yl)propenoic acid, t-butyl ester

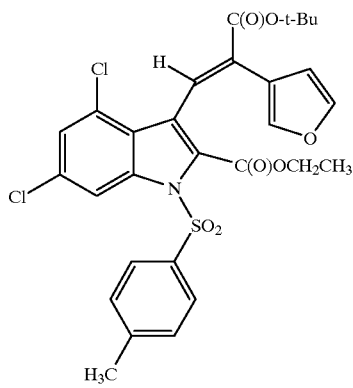

Prepare by a method similar to Example 3.1 using furan-3-boronic acid to give the title compound.

4.2 Synthesis of (E)-2-(Fur-3-yl)-3-(1-p-toluenesulfonyl-2-carboethoxy-4,6-dichloroindol-3-yl)propenoic acid

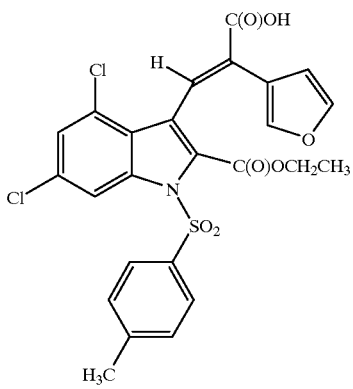

Prepare by a method similar to Example 3.2 using (E)-2-(fur-3-yl)-3-(1-p-toluenesulfonyl-2-carboethoxy-4,6-dichloroindol-3-yl)propenoic acid, t-butyl ester to give the title compound.

4.3 Synthesis of (E)-2-(Fur-3-yl)-3-(4,6-dichloroindol-3-yl-2-carboxylic acid)propenoic acid

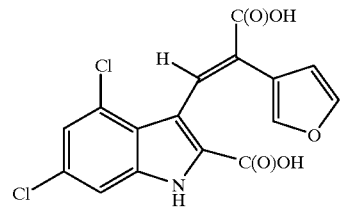

Prepare by a method similar to Example 3.3 using (E)-2-(fur-3-yl)-3-(1-p-toluenesulfonyl-2-carboethoxy-4,6-dichloroindol-3-yl)propenoic acid to give the title compound: mp; 223–225° C. (dec). $^1$H NMR (DMSO-$d_6$) δ 13.0 (bs, 2H), 12.35 (s, 1H), 7.94 (s, 1H), 7.48 (m, 1H), 7.42 (d, 1H, J=1.7 Hz), 7.34 (m, 1H), 7.15 (d, 1H, J=1.7 Hz), 5.77 (m, 1H).

EXAMPLE 5

Preparation of (E)-2-(Pyrid-3-yl)-3-(4,6-dichloroindol-3-yl-2-carboxylic acid)propenoic acid

5.1 Synthesis of (Z)-2-(Pyrid-3-yl)-3-(2-carboethoxy-4,6-dichloroindol-3-yl)propenonitrile

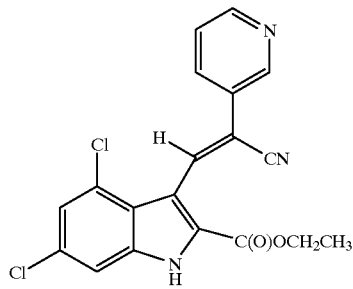

Combine 2-carboethoxy-4,6-dichloroindole (1.43 g, 5.0 mmol), pyrid-3-ylacetonitrile (0.59 g, 5.0 mmol), piperidine (0.2 mL), and ethanol (30 mL). Heat to reflux. After 16 hours, cool to ambient temperature. Add diethyl ether to give a solid. Filter, rinse with diethyl ether, dry, recrystallize from acetone/water, filter, and dry to give the title compound: mp; 233–234° C. (dec). $^1$H NMR (DMSO-$d_6$) δ 12.41 (br s, 1H), 8.86 (s, 1H), 8.57 (d, 1H, J=1 Hz), 8.16 (s, 1H), 7.94 (d, 1H, J=6.1 Hz), 7.41–7.36 (m, 1H), 7.41 (s, 1H), 7.06 (m, 1H), 4.30 (q, 2H, J=7.05 Hz), 1.23 (t, 3H, J=7.05 Hz).

5.2 Synthesis of (Z)-2-(Pyrid-3-yl)-3-(4,6-dichloroindol-3-yl-2-carboxylic acid)propenoic acid imide

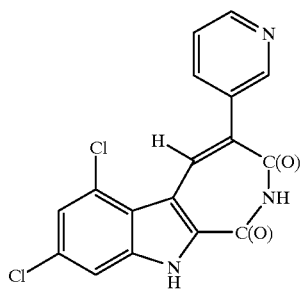

Combine (Z)-2-(pyrid-3-yl)-3-(2-carboethoxy-4,6-dichloroindol-3-yl)propenonitrile (0.5 g, 1.3 mmol), sulfuric acid (6 mL), acetic acid (6 mL), and water (0.3 mL). Heat to about 80° C. After 16 hours, pour the reaction mixture onto water to give a solid. Filter the solid and combine with lithium hydroxide (91.0 mg, 2.6 mmol) in tetrahydrofuran/water (1/1, 10 mL) and heat to 60° C. After 16 hours, filter the solid and recrystallize from acetone/water give the title compound. $^1$H NMR (300 MHz, DMSO-$d_6$) δ 13.25 (s, 1H, NH), 11.92 (s, 1H, NH), 8.66 (m, 1H), 8.57 (m, 1H), 8.43 (s, 1H), 7.91 (m, 1H), 7.57 (s, 1H), 7.45 (s overlapping m, 2H).

5.3 Synthesis of (E)-2-(Pyrid-3-yl)-3-(4,6-dichloroindol-3-yl-2-carboxylic acid)propenoic acid

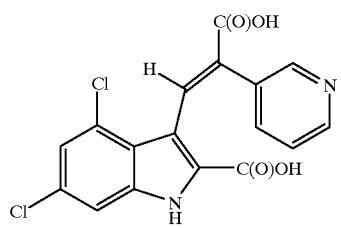

Combine (Z)-2-(pyrid-3-yl)-3-(4,6-dichloroindol-3-yl-2-carboxylic acid)propenoic acid imide (152 mg, 0.43 mmol), aqueous 6 M sodium hydroxide solution (6 mL), and tetrahydrofuran (2 mL). Heat to 60° C. After 48 hours, cool the reaction mixture to ambient temperature and evaporate in vacuo to remove the tetrahydrofuran. Dilute the reaction mixture with water (20 mL) and acidify to pH 2 with aqueous 12 M hydrochloric acid solution to give a solid. Filter, rise with water, and dry to give the title compound: mp 285–286° C. (dec). $^1$H NMR (300 MHz, DMSO-$d_6$) δ 13.18 (br m, 2H), 12.28 (s, 1H), 8.26 (m, 1H), 8.22 (s, 1H), 8.09 (m, 1H), 7.39 (d, 1H, J=1.8 Hz), 7.35 (s, 1H), 7.19 (s overlapping m, 2H).

EXAMPLE 6

Preparation of (E)-2-(Pyrid-2-yl)-3-(4,6-dichloroindol-3-yl-2-carboxylic acid)propenoic acid

6.1 Synthesis of (Z)-2-(Pyrid-2-yl)-3-(2-carboethoxy-4,6-dichloroindol-3-yl)propenonitrile

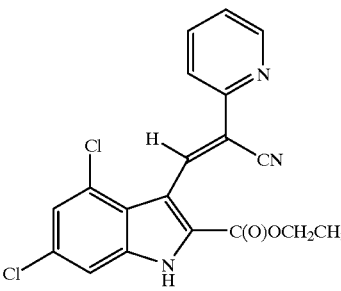

Combine 2-carboethoxy-4,6-dichloroindole (1.43 g, 5.0 mmol), pyrid-2-ylacetonitrile (0.59 g, 5.0 mmol), piperidine (0.2 mL), and ethanol (30 mL). Heat to reflux. After 16 hours, cool to ambient temperature. Add diethyl ether to give a solid. Filter, rinse with diethyl ether, dry, recrystallize from acetone/water, filter, and dry to give the title compound: mp; 250–254° C. (dec). $^1$H NMR (DMSO-$d_6$) δ 12.9 (br s, 1H), 8.86 (s, 1H), 8.70 (d, 1H, J=1 Hz), 8.00 (m, 1H), 7.82 (d, 1H, J=7.2 Hz), 7.55 (s, 1H), 7.48 (m, 1H), 7.48 (m, 1H), 7.34 (s, 1H), 4.35 (q, 2H, J=7.1 Hz), 1.25 (t, 3H, J=7.1 Hz).

6.2 Synthesis of (Z)-2-(Pyrid-2-yl)-3-(4,6-dichloroindol-3-yl-2-carboxylic acid)propenoic acid imide

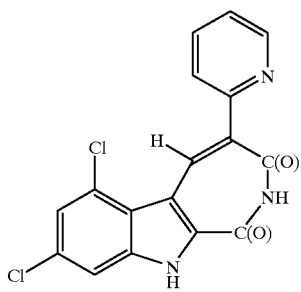

Combine (Z)-2-(pyrid-2-yl)-3-(2-carboethoxy-4,6-dichloroindol-3-yl)propenonitrile (1.0 g, 2.6 mmol), sulfuric acid (15 mL), acetic acid (15 mL), and water (0.3 mL). Heat to about 80° C. After 16 hours, cool to ambient temperature and pour the reaction mixture into water (50 mL) to obtain a solid. Filter the solid, rinse with water. Recrystallize from acetone/water, filter, and dry to give the title compound as the sulfuric acid salt: mp; >300° C. $^1$H NMR (DMSO-$d_6$) δ 13.47 (br s, 1H), 12.14 (m, 1H), 8.90–8.83 (m, 1H), 8.83 (s, 1H), 8.02 (d, 1H, J=7.7 Hz), 7.81 (m, 1H), 7.60 (s, 1H), 7.43 (s, 1H), 7.48 (m, 1H), 7.34 (s, 1H).

Combine (Z)-2-(pyrid-2-yl)-3-(4,6-dichloroindol-3-yl-2-carboxylic acid)propenoic acid imide sulfuric acid salt (285 mg, 0.65 mmol), lithium hydroxide (67 mg, 1.6 mmol), and tetrahydrofuran/water (1/1, 10 mL). Heat at 60° C. After 16 hours, filter, rinse with water, and dry to give the title compound.

6.3 Synthesis of (E)-2-(Pyrid-2-yl)-3-(4,6-dichloroindol-3-yl-2-carboxylic acid)propenoic acid

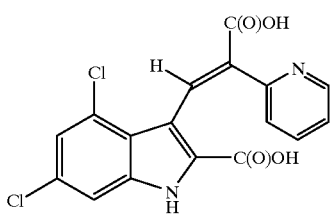

Prepare by a method similar to Example 5.3 using (Z)-2-(pyrid-2-yl)-3-(4,6-dichloroindol-3-yl-2-carboxylic acid)propenoic acid imide (0.5 g, 1.3 mmol) to give the title compound.

EXAMPLE 7

Preparation of (E)-2-(Pyrid-4-yl)-3-(4,6-dichloroindol-3-yl-2-carboxylic acid)propenoic acid

7.1 Synthesis of (Z)-2-(Pyrid-4-yl)-3-(2-carboethoxy-4,6-dichloroindol-3-yl)propenonitrile

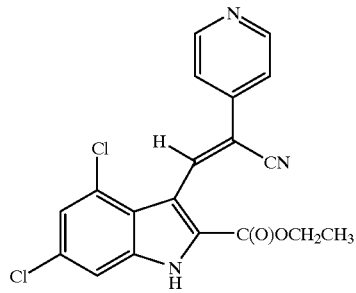

Prepare by a method similar to Example 5.1 using pyrid-4-ylacetonitrile hydrochloride salt and triethylamine to give the title compound: mp; 265° C. (dec). 1H NMR (DMSO-$d_6$) δ 11.97 (br s, 1H), 8.74 (m, 3H), 7.76 (d, 2H, J=4.7 Hz), 7.56 (s, 1H), 7.39 (m, 1H), 4.35 (q, 2H, J=6.8 Hz), 1.24 (t, 3H, J=6.8 Hz).

7.2 Synthesis of (Z)-2-(Pyrid-4-yl)-3-(4,6-dichloroindol-3-yl-2-carboxylic acid)propenoic acid imide

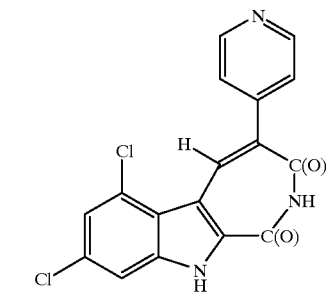

Prepare by a method similar to Example 5.2 using (Z)-2-(pyrid-4-yl)-2-carboethoxy-4,6-dichloroindol-3-yl)propenonitrile to give the title compound.

7.3 Synthesis of (E)-2-(Pyrid-4-yl)-3-(4,6-dichloroindol-3-yl-2-carboxylic acid)propenoic acid

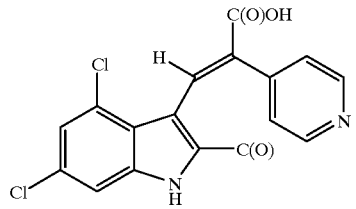

Prepared by a method similar to Example 5.3 using (Z)-2-(pyrid-4-yl)-3-(4,6-dichloroindol-3-yl-2-carboxylic acid)propenoic acid imide to give the title compound.

EXAMPLE 8

Preparation of (E)-2-(Thien-2-yl)-3-methyl-3-(indol-3-yl-2-carboxylic acid)propenoic acid

8.1 Synthesis of (E)-2-(Thien-2-yl)-3-methyl-3-(1-p-toluenesulfonyl-2-carboethoxy-indol-3-yl) propenoic acid, t-butyl ester

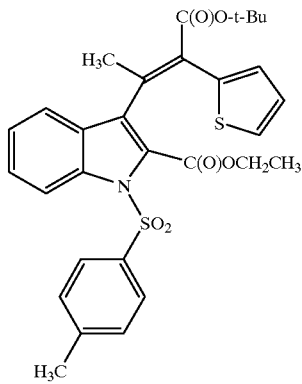

Prepare by the method of Example 2.1 using (Z)-2-bromo-3-methyl-3-(1-p-toluenesulfonyl-2-carboethoxyindol-3-yl)propenoic acid, t-butyl ester to give the title compound.

8.2 Synthesis of (E)-2-(Thien-2-yl)-3-methyl-3-(1-p-toluenesulfonyl-2-carboethoxy-indol-3-yl) propenoic acid

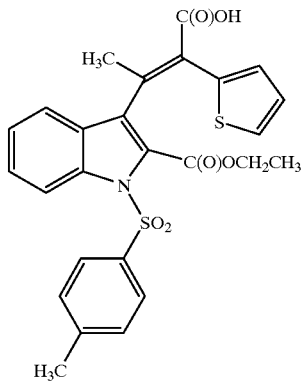

Prepare by the method of Example 2.2 using (E)-2-(thien-2-yl)-3-methyl-3-(1-p-toluenesulfonyl-2-carboethoxyindol-3-yl)propenoic acid, t-butyl ester to give the title compound.

8.3 Synthesis of (E) and (Z)-2-(Thien-2-yl)-3-methyl-3-(indol-3-yl-2-carboxylic acid)propenoic acid

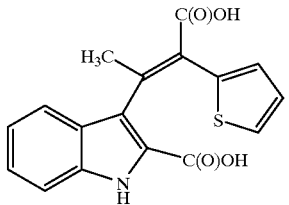

Prepare by the method of Example 2.3 using (E) and (Z)-2-(thien-2-yl)-3-methyl-3-(1-p-toluenesulfonyl-2-carboethoxy-indol-3-yl)propenoic acid to give the title compound.

The compounds of Formula (I) are excitatory amino acid antagonists. They antagonize the effects which excitatory amino acids have upon the NMDA receptor complex. They preferentially bind to the strychnine-insensitive glycine binding site on the NMDA receptor complex associated with the treatment of a number of disease states. See Palfreyman, M. G. and B. M. Baron, *Excitatory Amino Acid Antagonists*, B. S. Meldrum ed., Blackwell Scientific, 101–129 (1991); and, Kemp, J. A., and P. D. Leeson, *Trends in Pharmacological Sciences*, 14, 20–25 (1993).

Affinity for brain strychnine-insensitive glycine binding site on the NMDA receptor complex can be determined in the following way. Approximately 50 to 60 young male Sprague-Dawley rats (C-D strain), are sacrificed by decapitation and their cerebral cortices and hippocampi are removed. The two brain regions are combined and homogenized in 15 volumes of ice-cold 0.32 M sucrose using a teflon glass homogenizer (10 passes at 400 rpm). The homogenates are centrifuged at 1000×g for 10 minutes and the supernatants are transferred and recentrifuged at 44,000×g for 20 minutes. The upper white part of the pellets are resuspended with a pipet in ice-cold water and homogenized with a polytron (setting 6 for 10 seconds) and centrifuged at 44,000×g for 15 minutes. Pellets are then resuspended in 6 volumes of water and placed in a dry-ice/methanol bath until frozen, followed by thawing at 37° C. in a shaking water bath. The freeze/thaw process is repeated and final volumes of the suspensions adjusted to 15 volumes with water and centrifuged at 44,000×g for 15 minutes. The resulting pellets are resuspended in 15 volumes of 10 mM HEPES-KOH (N-2-hydroxyethyl-piperazine-N'-2-ethanesulsonic acid-potassium hydroxide) at pH 7.4 containing 0.04% Triton X-100 (v/v), incubated at 37° C. for 15 minutes and centrifuged at 44,000×g for 15 minutes. The pellets are then resuspended in 15 volumes of 10 mM HEPES-KOH at pH 7.4 with a polytron (setting of 6 for 10 seconds) and centrifuged at 44,000×g for 15 minutes. Repeat this resuspension/centrifugation process an additional 2 times. The membranes are then resuspended in 3 volumes of 10 mM HEPES and stored frozen at −80° C.

When the assay is to be performed, the membranes are thawed at ambient temperature and diluted with 9 volumes of 10 mM HEPES-KOH pH 7.4 and incubated at 25° C. for 15 minutes This is followed by centrifugation at 44,000×g for 15 minutes then resuspension with 10 mM HEPES-KOH at pH 7.4 using a polytron. The incubation/resuspension/centrifugation process is repeated an additional 2 times and the final pellet is resuspended in 6 volumes of 50 mM HEPES-KOH at pH 7.4. Incubation vials in triplicate, receive 50 μL of 200 nM [$^3$H]-glycine, 50 μL of 1000 nM strychnine, 50 μL of various concentrations of test compounds diluted with 50 mM HEPES-KOH at pH 7.4, and 200 μL of membrane suspension (400 μg protein/aliquot) in a final volume of 0.5 mL. Incubations are carried out at 4° C. for 30 minutes and are terminated by centrifugation at 46,000×g for 10 minutes. The supernatants are decanted and the pellets are rinsed rapidly with 2 mL of ice-cold 50 mM HEPES-KOH at pH 7.4, then dissolved in 4 mL of Ready Protein (Beckman Instruments) and counted by liquid scintillation spectrometry.

Specific binding of [$^3$H]-glycine is measured as the total radioactivity bound minus that bound to the receptors in the presence of 0.1 mM M D-serine. Total membrane-bound radioactivity is less that 2% of that added to the assay vials. Since these conditions limit the total binding to less than 10% of the radioactivity, the concentration of free ligand does not change appreciably during the assay. The results of this assay are expressed as an IC$_{50}$, that is the molar concentration of a compound which causes 50% inhibition of ligand binding.

| Compound No. | Binding to the strychnine-insensitive glycine binding site on the NMDA receptor complex, IC$_{50}$, |
|---|---|
| 1 | 5.25 |
| 2 | 9.0 |
| 3 | 22 |
| 4 | 21 |

Compound No. 1 is the compound of Example 1, (E) and (Z)-2-(Thien-3-yl)-3-(4,6-dichloroindol-3-yl-2-carboxylic acid)propenoic acid;

Compound No. 2 is the compound of Example 2, (E) and (Z)-2-(Thien-2-yl)-3-(4,6-dichloroindol-3-yl-2-carboxylic acid)propenoic acid;

Compound No. 3 is the compound of Example 3, (E) and (Z)-2-(Fur-2-yl)-3-(4,6-dichloroindol-3-yl-2-carboxylic acid)propenoic acid;

Compound No. 3 is the compound of Example 3, (E) and (Z)-2-(Fur-3-yl)-3-(4,6-dichloroindol-3-yl-2-carboxylic acid)propenoic acid.

The compounds exhibit anticonvulsant properties and are useful in the treatment of grand mal seizures, petit mal seizures, psychomotor seizures, autonomic seizures, etc. One method of demonstrating their antiepileptic properties is by their ability to inhibit the seizures that are caused by the administration of quinolinic acid. This test can be conducted in the following manner.

One group containing ten mice are administered 0.01–100 micrograms of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of tonic seizures. The control group will have a statistically higher rate of tonic seizures than will the test group.

Another method of demonstrating the antiepileptic properties of these compounds is by their ability to inhibit audiogenic convulsions in DBA/2J mice. This test can be conducted in the following manner. Typically one group of from 6–8 male DBA/2J audiogenic mice are administered from about 0.01 micrograms to about 10 micrograms of the test compound into the lateral ventricle of the brain or from about 0.1 milligrams to about 300 milligrams intraperitoneally. A second group of mice are administered an equal volume of a saline control by the same route. Five minutes to 4 hours later, the mice are placed individually in glass jars and are exposed to a sound of 110 decibels for 30 seconds. Each mouse is observed during the sound exposure for signs of seizure activity. The control group will have a statistically higher incidence of seizures than the group which receives the test compound.

The compounds of Formula (I) are useful for preventing or minimizing the damage which nervous tissues contained within the CNS suffer upon exposure to either ischemic, traumatic, or hypoglycemic conditions including strokes or cerebrovascular accidents, cardiovascular surgery, concussions, hyperinsulinemia, cardiac arrest, drownings, suffocations, and neonatal anoxic trauma. The compounds should be administered to the patient within 24 hours of the onset of the hypoxic, ischemic, traumatic, or hypoglycemic condition in order to minimize the CNS damage which the patient will experience.

The compounds of Formula (I) minimize or prevent CNS damage after ischemia. These anti-ischemia properties can be demonstrated by the ability of the compounds of Formula (I) to reduce infarct volume in rats subjected to middle cerebral artery occlusion as follows. Male Sprague-Dawley rats are subjected to occlusion of the middle cerebral artery by an adaptation of the method of H. Memezawa et al., *Ischemia Penumbra in a Model of Reversible Middle Cerebral Artery Occlusion in the Rat, Experimental Brain Research*, 89, 67–78 (1992). The rat is anesthetized with halothane in a mixture of O$_2$ and NO (1:2 ratio) and a midline incision is made in the ventral neck region. An indwelling venous catheter is placed in the jugular vein. Under a dissecting microscope, the left common carotid artery is identified at its bifurcation into the external carotid artery and internal carotid artery. Two ties are placed on the external carotid artery. The internal carotid artery is exposed distally to the point of its bifurcation into the intracranial internal carotid artery and the pterygopalatine artery. A small cut is made in the distal segment of the external carotid artery and a 3-0 nylon monofilament is introduced into the lumen of the external carotid artery. The two previously placed ties are tightened around the monofilament. The external carotid artery is cut and reflected caudally so that the monofilament can be advanced into the internal carotid artery, past the distal internal carotid artery/pterygopalatine artery bifurcation and continuing into the intranial segment of the internal carotid artery to a distance of 20 mm, at which point the origin of the middle cerebral artery is occluded. The ties are then tightened and the wound is closed. Compound or vehicle alone is administered intravenously at a pre-determined time post-ischemia and dosing can be single, multiple, or by continuous infusion.

Animals are given food and water and allowed to survive for 24 h. Prior to sacrifice, the rat is weighed and given a battery of four neurological tests to measure muscle strength, grooming skills, postural reflexes and sensorimotor integration, as described by C. G. Markgraf et al., *Sensorimotor and Cognitive Consequences of Middle Cerebral Artery Occlusion in Rats, Brain Research*, 575, 238–246 (1992). The animal is then decapitated, the brain is removed, sliced into six sections and incubated in 2% 2,3,5-triphenyltetrazolium chloride for 30 minutes, as described by K. Isayama et al., *Evaluation of 2,3,5-Triphenyltetrazolium Chloride Stains to Delineate Rat Brain Infarcts, Stroke* 22, 1394–1398 (1991). The area of infarction is clearly visible. Infarct area is determined by computer-assisted image analysis for each of the six sections and integrated over the anterior-posterior extent of the brain to yield infarct volume. Group means ±SE are determined for infarct volume and for the four behavioral tests and compared for the groups using ANOVA with orthogonal contrasts.

Another method of demonstrating the ability of the compounds of Formula (I) minimize or prevent CNS damage after ischemia is as follows: An adult male rat weighing 200–300 g is anesthetized with halothane in a mixture of $O_2$ and NO (1:2 ratio) and a midline incision is made in the ventral neck region. An indwelling venous catheter is placed in the jugular vein. The common carotid artery is exposed and dissecte free from the vagus and cervical sympathetic nerves. One 4-0 silk suture ligature is tied securely. The animal is the placed in a restraint so that the right side of the head is facing up. The area is rubbed with betadiene and then the incision through the skin and the temporalis muscle is made in order to expose the skull. Care should be taken no to cut the large vein that is visible through the muscle. Once the skull is exposed the middle carotid artery is visble through the skull. Using a Foredom micro drill with a 4 mm burr bit, a small (approximatel 8 mm) hole is made in the skull directly above the middle carotid artery. After drilling through the skull there is usually a thin layer of skull remaining that is carefully removed with fine foreceps. Remove the dura, as required, away from the area directly above the middle carotid artery. The right middle cerebral artery occlusion is then performed by electrocoagulation without damaging the brain. The middle cerebral artery is cauterized immediately distal to the inferior cortical vein. A small piece of foam gel is then placed in the area and the muscle and skin in sutured with 3-0 silk. Compound or vehicle alone is administered intravenously at a predetermined time post-ischemia and dosing can be single, multiple, or by continuous infusion.

Animals are given food and water and allowed to survive for 24 h. The animal is then decapitated, the brain is removed, sliced into six sections and incubated in 2% 2,3,5-triphenyltetrazolium chloride for 30 minutes, as described by K. Isayama et al., *Evaluation of 2,3,5-Triphenyltetrazolium Chloride Stains to Delineate Rat Brain Infarcts, Stroke* 22, 1394–1398 (1991). The area of infarction is clearly visible. Infarct area is determined by computer-assisted image analysis for each of the six sections and integrated over the anterior-posterior extent of the brain to yield infarct volume. Group means±SE are determined for infarct volume and for the four behavioral tests and compared for the groups using ANOVA with orthogonal contrasts.

The compounds are also useful in the treatment of neurodegenerative diseases such as Huntington's disease, Alzheimer's disease, senile dementia, glutaric acidaemia type I, multi-infarct dementia, amyotrophic lateral sclerosis, and neuronal damage associated with uncontrolled seizures. The administration of these compounds to a patient experiencing such a condition will serve to either prevent the patient from experiencing further neurode-generation or it will decrease the rate at which the neurodegeneration occurs.

As is apparent to those skilled in the art, the compounds will not correct any CNS damage that has already occurred as the result of either disease, physical injury, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C. R., *Distress Vocalization in Rat Pups: A Simple Screening Method For Anxiolytic Drugs, J. Pharmacol. Methods*, 14, 181–87 (1986) and Insel et.al., *Rat Pup Isolation Calls: Possible Mediation by the Benzodiazepine Receptor Complex, Pharmacol. Biochem. Behav.*, 24, 1263–67 (1986).

The compounds also exhibit an analgesic effect and are useful in controlling pain. The compounds are also effective in the treatment of migraine.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically an effective dose of the compounds will range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a therapeutic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula (I) can be tableted with conventional tablet bases such as lactose, sucrose, and cornstarch, in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or nonaqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

As used in this application:
aa) the "patient" refers to warm blooded animals such as, for example guinea pigs, mice, rats, cats, rabbits, dogs, monkeys, chimpanzees, and human;
bb) the term "treat" refers to the ability of the compounds to either relieve, alleviate, or slow the progression of the patient's disease;
cc) the term "neurodegeneration" refers to a progressive death and disappearance of a population of nerve cells occurring in a manner characteristic of a particular disease state and leading to brain damage.

The compounds of Formula (I) may also be admixed with any inert carrier and utilized in laboratory assays in order to determine the concentration of the compound within the serum, urine, etc., of the patient as is known in the art.

Neurodegenerative diseases are typically associated with a loss of NMDA receptors. Thus, the compounds of Formula (I) may be utilized in diagnostic procedures to aid physicians with the diagnosis of neurodegenerative diseases. The compounds may be labeled with imaging agents known in the art such as isotopic ions and administered to a patient in order to determine whether the patient is exhibiting a decreased number of NMDA receptors and the rate at which that loss is occurring.

What is claimed is:

1. A method for blocking excitatory amino acid action in preventing seizures, said method comprising administering to a patient in need thereof, an effective amount of an NMDA receptor antagonistic of the formula:

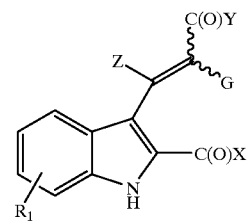

wherein
Z is hydrogen or —CH$_3$;
X is represented —OH;
Y is represented —OH;
R$_1$ is represented by from 1 to 3 substituents independently chosen from the group: hydrogen, C$_1$–C$_4$ alkyl, C$_1$–C$_4$ alkoxy, halogen, —CF$_3$, or —OCF$_3$;
G is a radical chosen from the group

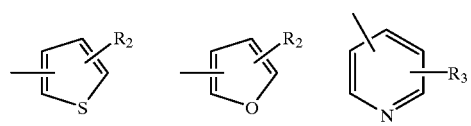

wherein
R$_2$ is represented by from 1 to 2 substituents independently chosen from the group: hydrogen or C$_1$–C$_4$ alkyl;
R$_3$ is represented by from 1 to 2 substituents independently chosen from the group: hydrogen, C$_1$–C$_4$ alkyl, C$_1$–C$_4$ alkoxy, or halogen;
and pharmaceutically acceptable addition salts thereof.

2. A method for blocking excitatory amino acid action in preventing Huntington's disease, Alzheimer's disease, senile dementia, glutaric acidaemia type I, multi-infarct dementia, amyotrophic lateral sclerosis or neuronal damage associated with seizures, said method comprising administering to a patient in need thereof, an effective amount of an NMDA receptor antagonistic of the formula:

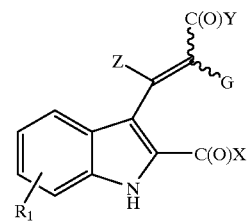

wherein
Z is hydrogen or —CH$_3$;
X is represented —OH;
Y is represented —OH;

$R_1$ is represented by from 1 to 3 substituents independently chosen from the group: hydrogen, $C_1$–$C_4$ alkyl, $C_1$–$C_4$ alkoxy, halogen, —$CF_3$, or —$OCF_3$;

G is a radical chosen from the group

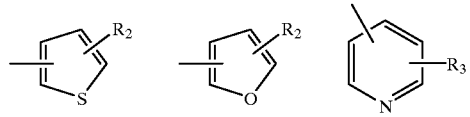

wherein $R_2$ is represented by from 1 to 2 substituents independently chosen from the group: hydrogen or $C_1$–$C_4$ alkyl;

$R_3$ is represented by from 1 to 2 substituents independently chosen from the group: hydrogen, $C_1$–$C_4$ alkyl, $C_1$–$C_4$ alkoxy, or halogen;

and pharmaceutically acceptable addition salts thereof.

3. A method for blocking excitatory amino acid action in preventing ischemic, hypoxic or hypoglycemic damage to cerebral tissue, said method comprising administering to a patient in need thereof, an effective amount of an NMDA receptor antagonistic of the formula:

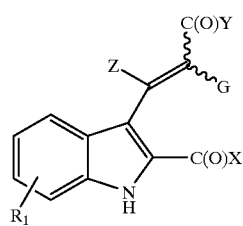

wherein

Z is hydrogen or —$CH_3$;

X is represented —OH;

Y is represented —OH;

$R_1$ is represented by from 1 to 3 substituents independently chosen from the group: hydrogen, $C_1$–$C_4$ alkyl, $C_1$–$C_4$ alkoxy, halogen, —$CF_3$, or —$OCF_3$;

G is a radical chosen from the group

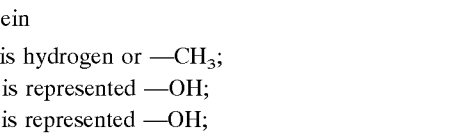

wherein $R_2$ is represented by from 1 to 2 substituents independently chosen from the group: hydrogen or $C_1$–$C_4$ alkyl;

$R_3$ is represented by from 1 to 2 substituents independently chosen from the group: hydrogen, $C_1$–$C_4$ alkyl, $C_1$–$C_4$ alkoxy, or halogen;

and pharmaceutically acceptable addition salts thereof.

4. A method for blocking excitatory amino acid action in treating anxiety, said method comprising administering to a patient in need thereof, an effective amount of a compound of the formula:

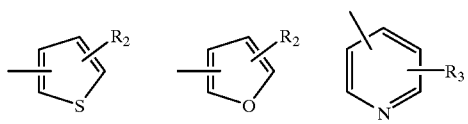

wherein

Z is hydrogen or —$CH_3$;

X is represented —OH;

Y is represented —OH;

$R_1$ is represented by from 1 to 3 substituents independently chosen from the group: hydrogen, $C_1$–$C_4$ alkyl, $C_1$–$C_4$ alkoxy, halogen, —$CF_3$, or —$OCF_3$;

G is a radical chosen from the group

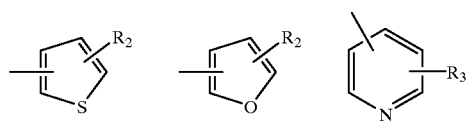

wherein $R_2$ is represented by from 1 to 2 substituents independently chosen from the group: hydrogen or $C_1$–$C_4$ alkyl;

$R_3$ is represented by from 1 to 2 substituents independently chosen from the group: hydrogen, $C_1$–$C_4$ alkyl, $C_1$–$C_4$ alkoxy, or halogen;

and pharmaceutically acceptable addition salts thereof.

5. A method for blocking excitatory amino acid action in controlling pain, said method comprising administering to a patient in need thereof, an effective analgesic amount of a compound of the formula:

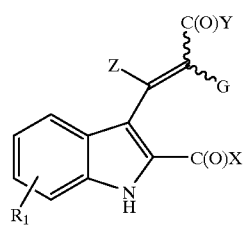

wherein

Z is hydrogen or —$CH_3$;

X is represented —OH;

Y is represented —OH;

$R_1$ is represented by from 1 to 3 substituents independently chosen from the group: hydrogen, $C_1$–$C_4$ alkyl, $C_1$–$C_4$ alkoxy, halogen, —$CF_3$, or —$OCF_3$;

G is a radical chosen from the group
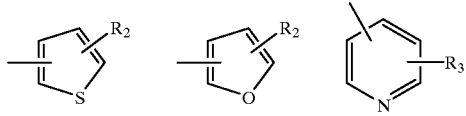
wherein
$R_2$ is represented by from 1 to 2 substituents independently chosen from the group: hydrogen or $C_1$–$C_4$ alkyl;
$R_3$ is represented by from 1 to 2 substituents independently chosen from the group: hydrogen, $C_1$–$C_4$ alkyl, $C_1$–$C_4$ alkoxy, or halogen;
and pharmaceutically acceptable addition salts thereof.
* * * * *